United States Patent
Popp

[11] Patent Number: 5,567,866
[45] Date of Patent: Oct. 22, 1996

[54] SIDE LOAD TESTER

[75] Inventor: Victor A. Popp, Hingham, Mass.

[73] Assignee: Instron Corporation, Canton, Mass.

[21] Appl. No.: 324,627

[22] Filed: Oct. 18, 1994

Related U.S. Application Data

[63] Continuation of Ser. No. 916,341, Jul. 17, 1992, abandoned.

[51] Int. Cl.6 ........................................................ G01N 3/00
[52] U.S. Cl. ............................................. 73/11.09; 73/669
[58] Field of Search ................................ 73/833, 859, 860, 73/808, 816, 11.04, 11.07, 11.08, 11.09, 669; 92/92, 93

[56] References Cited

U.S. PATENT DOCUMENTS

| | | | |
|---|---|---|---|
| 3,835,698 | 9/1974 | Zappia | 73/860 |
| 4,194,402 | 3/1980 | DeNicola | 73/859 |
| 4,888,995 | 12/1989 | Curtis . | |
| 5,224,386 | 7/1993 | Curtis | 73/833 |

*Primary Examiner*—Richard Chilcot
*Assistant Examiner*—Ronald L. Biegel

[57] ABSTRACT

A side load device for testing, for example, shock absorbers, in which an air actuator selectively moves an element to impose a side force on a product under test.

7 Claims, 1 Drawing Sheet

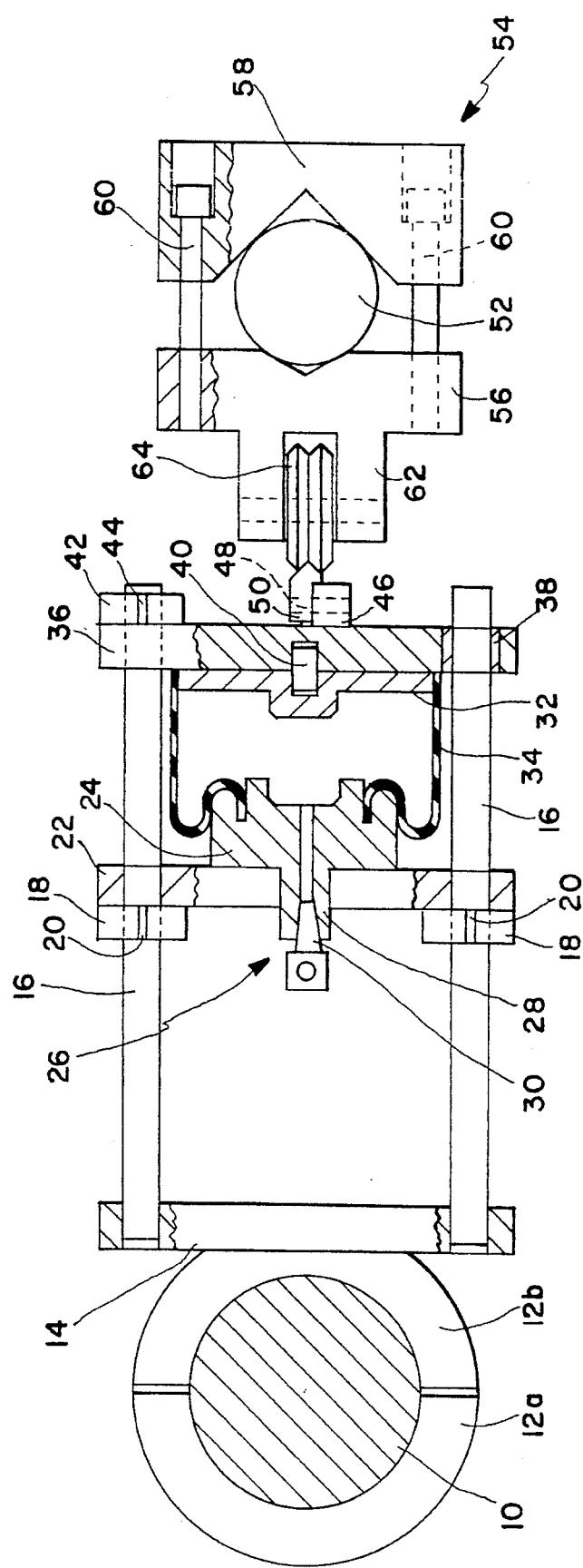

SIDE LOAD TESTER

This is a continuation of application Ser. No. 07/916,341, filed Jul. 17, 1992, now abandoned.

FIELD OF THE INVENTION

This invention relates to side load testing, as of shock absorbers for in-use life expectancy.

BACKGROUND OF THE INVENTION

It is known to test, for example, shock absorbers for life in use by repeatedly moving inner spring-loaded elements relative to outer housings, at predetermined cycling frequency, while imposing a predetermined side force on them.

Two types of prior art device supplied a collar around the shock absorber and applied a side force by a sidewise pulling on the collar through a cable. In one, the cable was put in tension by a weight, to which it ran over a pulley. In the other, the tension was applied hydraulically.

SUMMARY OF THE INVENTION

I have discovered that side loads may be desirably provided in testers by controlling fluid pressure to compressively drive a force member against a shock absorber or other device under test.

DRAWINGS

The FIGURE is a plan view, partially in section, of the presently preferred embodiment.

PREFERRED EMBODIMENT

The presently preferred embodiment is as now described in structure and operation.

Structure

The tester illustrated in the drawing is supported on vertical rod 10 by split collar 12a, 12b, the halves 12a and 12b of which are biased toward each other in gripping relation around rod 10 by threaded fasteners (not shown).

Split collar portion 12b is fixedly secured to base plate 14 by threaded fasteners (not shown).

Base plate 14 has secured in it, spaced 90° apart therearound, four horizontal cylindrical columns 16. Adjacent each column 16 base plate 14 is relieved in a slot therethrough extending from the periphery of the base plate to the column (not shown), and a threaded fastener (not shown) cooperates with the two portions of the base plate on opposite sides of the slot, and adjacent the column, to enable clamping in the same manner as split collar 12a, 12b.

Horizontal columns 16 extend next through four collars 18, each of which includes slot 20 and threaded fastening means (not shown) extending therethrough adjacent a column 16 to clamp the respective collar 18 therearound.

Columns 16 extend next through stationary platen plate 22, against which is seated a stationary portion 24 of the air actuator indicated generally at 26. Such air actuators are commercially available from Firestone Airmount Company, Carmel, Ind.

Part of portion 24 is projection 28, which extends through platen plate 22 and is fed by air supply connector 30. Air actuator 26 includes also movable plate 32 and elastomeric diaphragm 34.

Driven by movable plate 32 is movable platen 36, which is slidably mounted on columns 16 and includes self-lubricating fiberglass-reinforced teflon bearings 38, sold by Rexnord Corporation, Milwaukee, Wis., under the mark DURALON. Dowel 40 keeps plate 32 and platen 36 in alignment.

Secured around columns 16 adjacent movable platen 36 are four clamp rings 42, with slots 44 and fastening means (not shown) extending through the clamp rings and the slot, as with clamp rings 18, to clamp clamp rings 42 around columns 16.

Mounted on movable plate 36 by fastening means (not shown) is support member 46, which has secured thereto through a fastener (not shown) through portion 48 of flat (the outline of the cross-section shown extends in straight lines perpendicularly of the paper on which the FIGURE is drawn) V member 50.

Shock absorber 52 is held in a grip indicated generally at 54 with V-jaws 56 and 58 selectively clampable around a shock absorber by means of fasteners 60.

V-jaw 56 has rotatably mounted on projection 62 thereof V-roller 64, oriented to roll on flat V 50.

Shock absorber 52 is mounted, inner and outer longitudinally spaced portions, on clamping means (not shown) like those used in ordinary automobiles for their mounting.

Operation

In operation, with shock absorber 52 held as described at its longitudinally spaced inner and outer portions, and gripped in jaws 56, 58, the device of the invention is used, by imposing the desired air pressure inside diaphragm 34 through air from connector 30. This moves movable platen 36 and associated V-member 50 to provide that pressure. The position of the exertion of the force may be changed by moving clamp ring 12a, 12b, and if desired jaws 56, 58 as well. The two parts of the shock absorber may be longitudinally moved and returned, with a predetermined stroke of for example four inches, at a predetermined frequency. A load cell may if desired be used to measure dynamically longitudinal forces during this cycling, which may go on with a single shock absorber for days.

Movability of collars 18 on columns 16 permits adjustment of the location of stationary platen 22. In the same manner, clamps 42 limit the travel of movable platen 36.

Roller-V 64 rolls along rail-V 50 as one portion of the shock absorber moves longitudinally with respect to the other.

My side load tester has a number of advantages. It does not have the inertial disadvantages of the weight prior art above referred to. It is simpler and less expensive than the hydraulic prior art above referred to. My invention is inexpensive and has few moving parts. Its linear bearings may be used to prevent wobble. It desirably provides a highly uniform force over a large amplitude. It desirably provides good damping. It desirably has a very flat force:deflection characteristic. It desirably provides a constant force at any predetermined pressure.

OTHER EMBODIMENTS

Other embodiments of the invention will occur to those skilled in the art.

For example, the stationary and movable platens between which air isolator cushion unit 26 is mounted may be related for relative pivotal movement rather than for parallel movement.

I claim:

1. A tester for applying a predetermined side load to a device under test which comprises:

a mount for positioning said tester against movement, a first plate immovably connected with said mount, a movable second plate for reciprocal movement relative to said first plate along first line of direction, an air actuator therebetween for selectively moving said second plate relative to said first plate, said actuator including a stationary member, a movable member, and an elastomeric air bag therebetween, and grip for holding said device facilitating reciprocal movement of said grip and said device along a second line of direction, said second plate being slidably mounted on columns fixedly mounted in said first plate, and said air bag through said second plate causing continued maintenance of said predetermined side load on said device during said movement of said grip and said device along said second direction.

2. The tester of claim 1 in which said grip comprises a first jaw and a second jaw.

3. The tester of claim 2 in which said second plate and said first jaw carry relative movement means permitting relative movement therebetween perpendicularly of said sidewise movement.

4. The tester of claim 3 in which one of said second plate and said first jaw carries a flat V member and the other carries a cooperating roller V member.

5. The tester of claim 4 in which said first jaw carries said roller V member.

6. The tester of claim 5 which includes a positioning dowel extending between said movable member and said second plate.

7. The tester of claim 1 in which said first direction is perpendicular to said second direction.

* * * * *